US008318930B2

(12) United States Patent
Tyagi et al.

(10) Patent No.: US 8,318,930 B2
(45) Date of Patent: Nov. 27, 2012

(54) PROCESS FOR PREPARING POLYMORPHIC FORMS OF (S)-6-CHLORO-(CYCLOPROPYLETHYNYL)-1,4-DIHYDRO-4-(TRIFLUOROMETHYL)-2H-3,1-BENZOXAZIN-2-ONE

(75) Inventors: Om Dutt Tyagi, Andhra Pradesh (IN); Ramakoteswara Rao Jetti, Andhra Pradesh (IN); B. A. Ramireddy, Andhra Pradesh (IN)

(73) Assignee: Matrix Laboratories Limited, Andhra Pradesh (IN)

( * ) Notice: Subject to any disclaimer, the term of this patent is extended or adjusted under 35 U.S.C. 154(b) by 207 days.

(21) Appl. No.: 12/810,288

(22) PCT Filed: Dec. 24, 2008

(86) PCT No.: PCT/IN2008/000860
§ 371 (c)(1),
(2), (4) Date: Jun. 28, 2010

(87) PCT Pub. No.: WO2009/087679
PCT Pub. Date: Jul. 16, 2009

(65) Prior Publication Data
US 2010/0274007 A1    Oct. 28, 2010

(30) Foreign Application Priority Data
Dec. 24, 2007    (IN) .............................. 3080/CHE/2007

(51) Int. Cl.
*C07D 265/18*    (2006.01)
(52) U.S. Cl. ............................................. 544/92; 544/90
(58) Field of Classification Search .................. 544/92
See application file for complete search history.

(56) References Cited

U.S. PATENT DOCUMENTS

| 5,519,021 A | 5/1996 | Young et al. |
| 6,939,964 B2 | 9/2005 | Crocker et al. |
| 2006/0235008 A1 | 10/2006 | Parthasaradhi Reddy et al. |

FOREIGN PATENT DOCUMENTS

| WO | 98/33782 | 8/1998 |
| WO | WO 9833782 A1 * | 8/1998 |
| WO | 2006/040643 A2 | 4/2006 |
| WO | WO 2006040643 A2 * | 4/2006 |

* cited by examiner

*Primary Examiner* — Kahsay T Habte
(74) *Attorney, Agent, or Firm* — Workman Nydegger

(57) ABSTRACT

Disclosed herein is a novel process for preparing polymorphic Forms of (S)-6-chloro-(cyclopropylethynyl)-1,4-dihydro-4-(trifluoromethyl)-2H-3,1-benzoxazin-2-one referred as $M_1$, I, II, β, and ω.

11 Claims, 2 Drawing Sheets

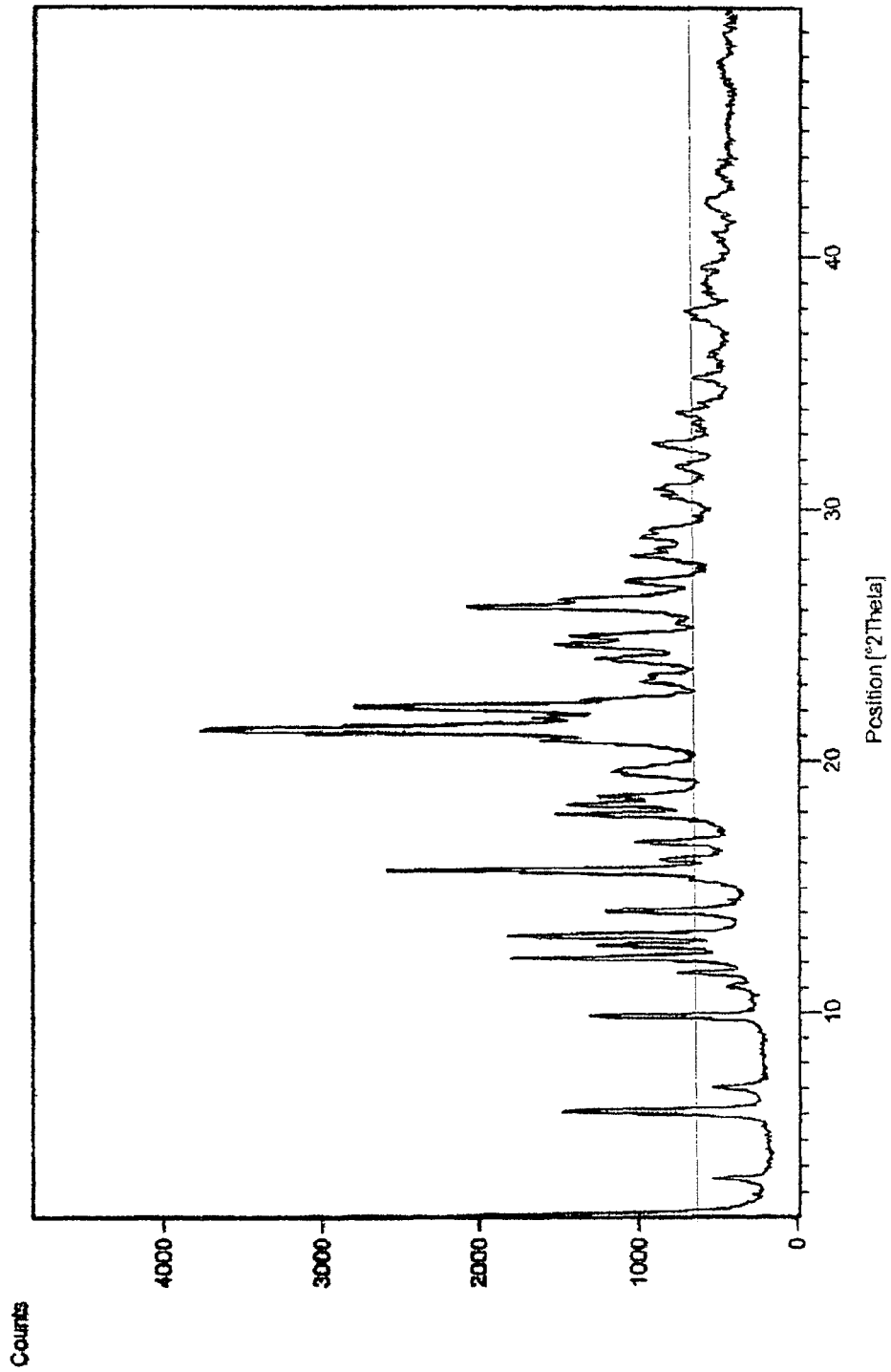
Fig. 1 Form M_I

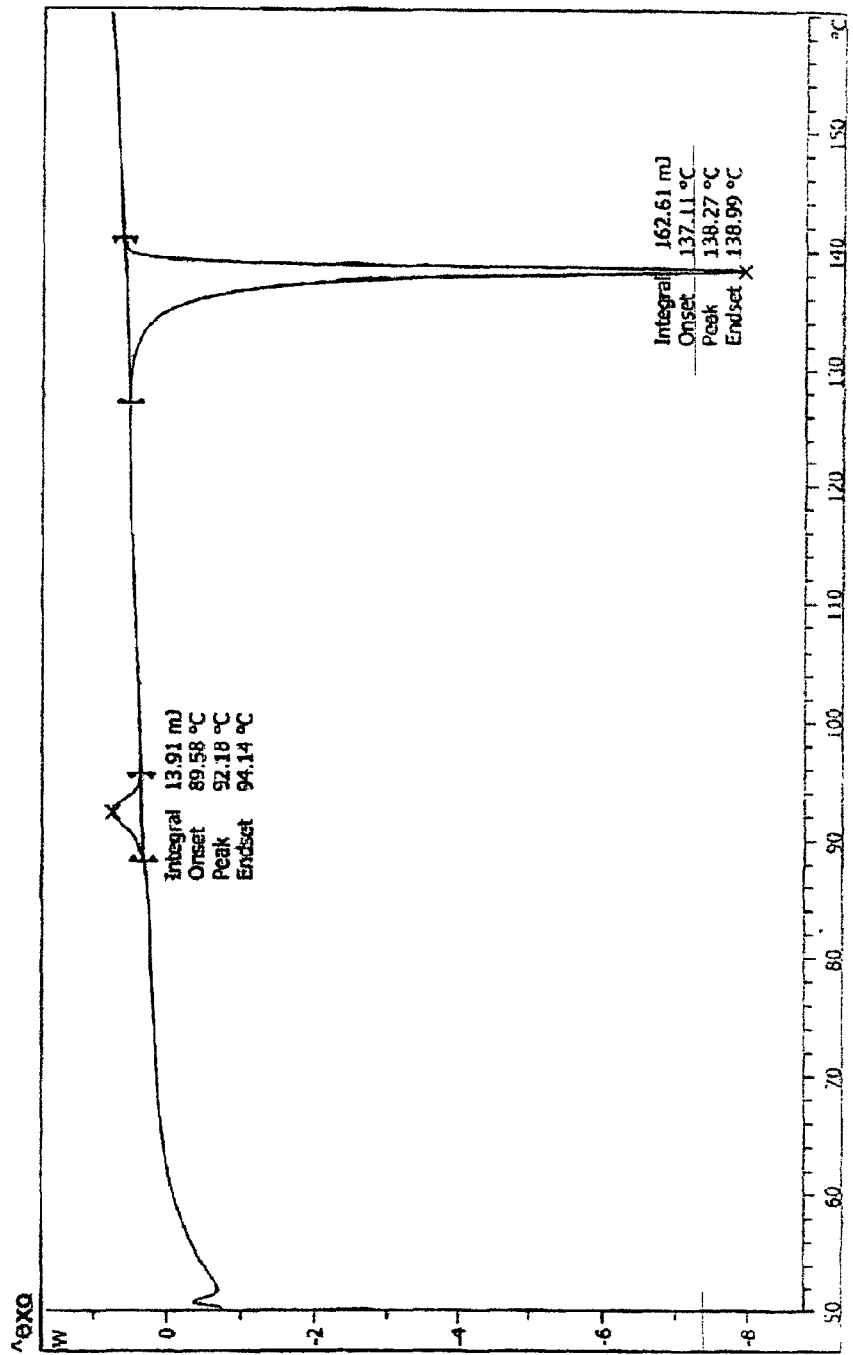
Fig. 2 (Form M₁)

PROCESS FOR PREPARING POLYMORPHIC FORMS OF (S)-6-CHLORO-(CYCLOPROPYLETHYNYL)-1,4-DIHYDRO-4-(TRIFLUOROMETHYL)-2H-3,1-BENZOXAZIN-2-ONE

FIELD OF THE INVENTION

This invention, in general, relates to a process for preparing polymorphic forms of (S)-6-chloro-(cyclopropylethynyl)-1,4-dihydro-4-(trifluoromethyl)-2H-3,1-benzoxazin-2-one (Efavirenz). More particularly, the present invention provides a novel process for preparing polymorphic Forms of efavirenz referred as $M_1$, I, II, β, and ω.

BACKGROUND OF THE INVENTION

Efavirenz is a non-nucleoside reverse transcriptase inhibitor (NNRTI) and is used as part of highly active antiretroviral therapy (HAART) for the treatment of a human immunodeficiency virus (HIV) type 1. Efavirenz is also used in combination with other antiretroviral agents as part of an expanded postexposure prophylaxis regimen to prevent HIV transmission for those exposed to materials associated with a high risk for HIV transmission.

Efavirenz, is chemically described as (S)-6-chloro-(cyclopropylethynyl)-1,4-dihydro-4-(trifluoromethyl)-2H-3,1-benzoxazin-2-one, having the following structure:

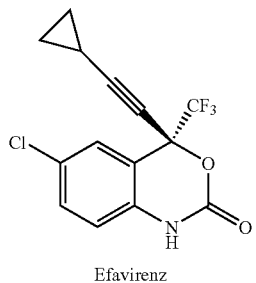

Efavirenz

Efavirenz product is first claimed in U.S. Pat. No. 5,519,021. The process disclosed in this patent involves reaction of racemic Efavirenz with optically active acid derivative followed by repeated purifications to give diastereomer. It is further subjected to hydrolysis in the presence of acid in n-butanol to give crude Efavirenz which is then recrystallized from hexane to give pure Efavirenz. However, this patent does not disclose any polymorphic forms of Efavirenz.

U.S. Pat. Nos. 6,939,964 and 6,639,071 claimed crystalline efavirenz polymorphic Forms I, II and III. U.S. Pat. No. 6,673,372 patent disclosed the crystalline efavirenz polymorphic Forms 1, 2, 3, 4 & 5. US 2006/0235008 claims different crystalline and amorphous forms of Efavirenz and process for the preparation thereof.

WO 2006/040643 application further discloses Efavirenz polymorphic Forms α, β, γ, γ1, γ2, ω, δ, N, O, P and processes for their preparation. The reproduction of examples for these polymorphs as disclosed in WO '643 is found to be very inconsistent. Also, it was found that some of these forms were never reproduced in our laboratory.

In light of above disadvantages in prior art processes, there is a need to prepare the pure and stable Efavirenz polymorphic forms by an efficient, economic and reproducible process, particularly to large scale preparation. Further, it should be suitable for handling and should have excellent physical and chemical stability, mainly to different heat and humidity conditions.

SUMMARY OF THE INVENTION

In accordance with prinicipal aspect of the present invention, there is provided a novel process for preparing polymorphic Forms of efavirenz, referred as $M_1$, I, II, β, and ω, wherein said process enables to achieve high purity and stability of said polymorphic forms.

In accordance with one preferred embodiment of the present invention, there is provided a novel process for preparing a polymorphic Form β of (S)-6-chloro-(cyclopropylethynyl)-1,4-dihydro-4-(trifluoromethyl)-2H-3,1-benzoxazin-2-one (Efavirenz), wherein the process comprises of dissolving efavirenz in a solvent, cooling the reaction mass followed by seeding the resultant, adding anti-solvent and isolating the pure efavirenz polymorphic Form β As is well-known in the art, an "anti-solvent" is a solvent in which a product is insoluble. When added to a solution containing a product, it reduces the solubility of the desired product and causes precipitation of the product.

In accordance with another preferred embodiment of the present invention, there is provided a novel process for preparing a polymorphic Form β of (S)-6-chloro-(cyclopropylethynyl)-1,4-dihydro-4-(trifluoromethyl)-2H-3,1-benzoxazin-2-one (Efavirenz), wherein the process comprises of dissolving the efavirenz in a mixture of water and water miscible organic solvent, removing the solvent and isolating the efavirenz polymorphic Form β, wherein the solvent is removed by employing freeze drying or distillation method.

BRIEF DESCRIPTION OF THE DRAWINGS

Further objects of the present invention together with additional features contributing thereto and advantages accruing there from will be apparent from the following description of preferred embodiments of the invention which are shown in the accompanying drawing figures, wherein:

FIG. 1: X-ray powder diffraction pattern of Efavirenz Form $M_1$

FIG. 2: DSC of Efavirenz Form $M_1$

DETAILED DESCRIPTION OF THE INVENTION

While this specification concludes with claims particularly pointing out and distinctly claiming that, which is regarded as the invention, it is anticipated that the invention can be more readily understood through reading the following detailed description of the invention and study of the included examples.

The disclosed embodiment of the present invention deals with a novel and consistent process for preparing polymorphic forms of (S)-6-chloro-(cyclopropylethynyl)-1,4-dihydro-4-(trifluoromethyl)-2H-3,1-benzoxazin-2-one, referred as Form I, Form II, Form β and Form ω.

The present invention also discloses a novel polymorphic form of (S)-6-chloro-(cyclopropylethynyl)-1,4-dihydro-4-(trifluoromethyl)-2H-3,1-benzoxazin-2-one, referred as Form $M_1$ and process for preparing said polymorphic form.

According to the present invention, the polymorphs disclosed herein are further characterized by X-ray powder diffraction pattern (XRD), Thermogravimetric Analysis (TGA), Differential Scanning Calorimetry (DSC), and/or moisture content (MC).

Powder X-ray Diffraction (PXRD)

The PXRD measurements were carried out using PANalytical, X'Pert PRO powder diffractometer equipped with goniometer of θ/θ configuration and X'Celerator detector. The Cu-anode X-ray tube was operated at 40 kV and 30 mA.

The experiments were conducted over the 2θ range of 2.0°-50.0°, 0.030° step size and 50 seconds step time.

Differential Scanning Calorimetry (DSC)

The DSC measurements were carried out on Mettler Toledo 822 Star$^e$ instrument. The experiments were performed at a heating rate of 10.0° C./minute over a temperature range of 30° C.-200° C. purging with nitrogen at a flow rate of 50 ml/minute. Standard aluminum crucibles covered by lids with three pin holes were used.

According to the present invention the novel polymorphic form $M_1$ of efavirenz is characterized by PXRD as shown in FIG. 1 and DSC as shown in FIG. 2.

The present invention provides a novel process for preparing polymorphic Form $M_1$ of efavirenz, wherein said process comprises of dissolving efavirenz in a suitable solvent at a temperature range between 20-30° C., preferably at 25-30° C., cooling the resultant to 0-10° C., preferably 0-5° C. followed by the addition of water and isolating the efavirenz Form $M_1$. The solvent used herein for dissolution is selected from a group consisting of formic acid, pyridine or mixtures thereof with water.

In another embodiment, the present invention provides a process for preparing polymorphic Form I of efavirenz, wherein the process comprises of heating crystalline efavirenz Form $M_1$ at 70-80° C. under vacuum for several hours to obtain Form I of efavirenz.

In another embodiment of the present invention, there is provided a process for preparing polymorphic Form I of efavirenz, wherein said process comprises of dissolving efavirenz in a solvent selected from the group consisting of lower aliphatic carboxylic acids, chlorinated solvents, heteroaromatics, esters, or mixtures thereof, preferably selected from acetic acid, dichloromethane (DCM), pyridine, ethyl acetate or mixtures thereof with water followed by addition of n-heptane, water or mixtures thereof and recovering the crystalline efavirenz Form I using different crystallization methods like anti-solvent or slow or fast crystallization or by distillation method In an embodiment of the present invention, the anti-solvent can be selected from water, n-heptane and mixtures thereof.

The present invention also provides a process for preparing Form II of efavirenz, wherein said process comprises of dissolving efavirenz in n-butanol, cooling the resultant to 0-5° C. followed by addition of water to obtain efavirenz Form II.

Further embodiment of the present invention provides a novel process for preparing polymorphic Form β of efavirenz, wherein the process comprises of dissolving efavirenz in a solvent at room temperature, cooling the resultant solution followed by seeding the resultant solution, adding anti-solvent and isolating the pure efavirenz polymorphic Form β. The temperature used herein for dissolving the efavirenz is in the range of 20-30° C., preferably 25-30° C. The clear solution is then cooled to 0-10° C., preferably to 0-5° C. and then seeded (~4%) with efavirenz Form β in lots, preferably in 1-3 lots. The antisolvent is then added to the above solution over a period of 1-3 hours. The precipitated solid is filtered and dried to obtain polymorphic Form β of efavirenz The antisolvent used may be selected from water, n-heptane and mixtures thereof.

According to the present invention, the solvent used herein for the preparation of β form of efavirenz is selected from the group comprising lower aliphatic alcohols, lower aliphatic carboxylic acids, hetero aromatics, polar aprotic solvents, esters, aliphatic hydrocarbons, or mixtures thereof with water, preferably methanol (MeOH), ethanol (EtOH), isopropyl alcohol (IPA), formic acid, acetic acid, ethyl acetate (EtOAc), isopropyl acetate, dimethylformamide (DMF), 1-methyl-2-pyrrolidinone (NMP). According to the present invention, the anti solvent is selected from n-heptane, water or mixtures thereof.

In an alternative embodiment of the present invention, the β form of efavirenz is prepared by a process comprising of dissolving efavirenz in a mixture of acetone/water or methanol/water followed by lyophilization or freeze-drying.

The β form of efavirenz, according to the present invention, can also be prepared by slurring Form $M_1$ in heptane, Isopropyl ether (IPE), water or mixture thereof at ambient temperature for several hours.

The β form of efavirenz can also be prepared by exposing Form $M_1$ to relative humidity (RH>90%) at ambient temperature for several hours at ambient temperature.

According to the present invention the β form of efavirenz is prepared consistently by above said processes having higher purity and stability under different heat and humid conditions.

In another embodiment, the present invention provides a process for preparing polymorphic Form ω of efavirenz, wherein the process comprises of dissolving efavirenz in a mixture of methanol and water followed by lyophilization or freeze-drying.

In the foregoing, embodiments are described by way of below examples to illustrate the process of invention. However, these are not intended in any way to limit the scope of the present invention and several variants of these examples would be evident to person ordinarily skilled in the art.

EXAMPLE 1

Preparation of Polymorphic Form $M_1$ of Efavirenz

Efavirenz (3 g) was dissolved in formic acid (30 ml) and the resulting clear solution was cooled to about 0-5° C., stirred for 30 min. Then added 400 ml of DM Water slowly and maintained at 0-5° C., then filtered and dried at ambient temperature. The resulting crystalline solid was identified as Efavirenz Form $M_1$.

XRD of the dried sample showed it to be Form $M_1$

EXAMPLE 2

Preparation of Polymorphic Form $M_1$ of Efavirenz

Efavirenz (3 g) was dissolved in pyridine (20 ml and the resulting clear solution was cooled to about 0-5° C., stirred for 30 min. Then 400 ml of DM Water was added slowly and maintained for 1 hr at 0-5° C., then filtered and dried at ambient temperature. The resulting crystalline solid was identified as Efavirenz Form $M_1$.

XRD of the dried sample showed it to be Form $M_1$.

EXAMPLE 3

Preparation of β Form of Efavirenz:

2 g Efavirenz was dissolved in indicated solvents at the indicated volumes at 50-60° C. The resulting solution is then filtered through hy-flow bed to remove undissolved particulate. The resulting clear solution was then subjected to freeze drying (Model: Virtis Genesis SQ Freeze Dryer) at −104° C. and below 200 Torr vacuum. The results are shown in following Table 1.

TABLE 1

| Input | Solvents | Volume ratio (v/v) | Result |
|---|---|---|---|
| Efavirenz | Water:Acetone | 1:1.25 | Form β |
| | Water:Methanol | 1:1.5 | |
| | Methanol | 1:5 | |

EXAMPLE 4

Preparation of β Form of Efavirenz:

3g of Efavirenz was dissolved in indicated solvents at the indicated volumes at 25-30° C. and stirred for 30 min. The resulting solution was cooled to 0-5° C. and an indicated anti solvent at the indicated volumes are added slowly. The resulting reaction mass was stirred at 0-5° C. The solid is filtered and washed with 5 ml of indicated solvents. The wet solid was dried at 25-30° C. The results are shown in following Table 2.

TABLE 2

| Process | Input | Solvents | Volume ratio (v/v) | PXRD Result |
|---|---|---|---|---|
| Antisolvent | Efavirenz | Acetic acid:water | 1:20 | Form β |
| | | DMF:water | 1:14 | |
| | | NMP:water | 1:14 | |

EXAMPLE 5

Preparation of β Form of Efavirenz:

Efavirenz (3 g) is suspended in Ethyl acetate (30 ml) at room temperature. Stir for 15 min to get clear solution. Filtered through cotton and cooled the solution to 0-5° C. Seeds added to the clear solution at 0-5° C. To this solution n-heptane (400 ml) added in two lots, with addition of second lot of the seeds and stirred for 30 min at 0-5° C. Distilled to half of the volume, then cooled to 0-5° C. and maintained for 1 hour. Solid material formed was filtered and air-dried. The solid obtained was identified as Efavirenz Form β.

XRD of the dried sample showed it to be Form β

EXAMPLE 6

Preparation of β Form of Efavirenz:

Efavirenz (5 g) is suspended in methanol (50 ml) at room temperature. Stir for 15 min to get clear solution. Filtered through cotton and cooled the solution to 0-5° C. Seeds of form-β (approx. 4%) in two lots added to the clear solution and stirred for 30 min at 0-5° C. Added 1 lt of water in two lots; first 25 ml of water added to the solution at 0-5 ° C., followed by third lot of form β seeds under stirring. Added remaining water in 1-2 hour and maintained for 2 hours at 0-5° C. The solid material formed was filtered at 0-5° C. The solid obtained was identified as Efavirenz Form β.

XRD showed it to be Form β

EXAMPLE 7

Preparation of Form I of Efavirenz:

1 g of Efavirenz Form $M_1$ obtained as described above was kept in a static dryer and heated at 80° C. under vacuum for 15 hr. The resulting solid was identified as Efavirenz Form I.

XRD showed it to be Form I

EXAMPLE 8

Preparation of Form I of Efavirenz:

Taken 3 g of Efavirenz in formic acid (30 ml) and heated to 80° C. to obtain a clear solution. Cooled to room temperature and added water (100 ml) slowly for 15-30 min and maintained for 36 hrs at Room Temperature (RT) with agitation. The resulting white free flowing solid was filtered and identified as Efavirenz Form I.

XRD showed it to be Form I

EXAMPLE 9

Preparation of Form I of Efavirenz:

Taken Efavirenz (1 g) in pyridine (2 ml) and filtered to remove undissolved particulate. The resulting solution was kept in Petri dish for aerial drying. The solid obtained was identified as Efavirenz Form I.

XRD showed it to be Form I

EXAMPLE 10

Preparation of Form I of Efavirenz:

Taken Efavirenz (1 g) in dichloromethane (25 ml) at room temperature and the resulting clear solution was distilled completely under vacuum. The solid obtained was identified as Efavirenz Form I.

XRD showed it to be Form I

EXAMPLE 11

Preparation of Form I of Efavirenz:

Taken Efavirenz (3 g) in ethyl acetate (30 ml) and stirred for 15-30 min at room temperature. To the resulting solution added n-heptanel(300 ml) and stirred for 1 hr at room temperature. The resulting clear solution was distilled half of the volume of reaction mass and cooled to room temperature and filtered. The obtained solid was identified as Efavirenz Form I.

XRD showed it to be Form I

EXAMPLE 12

Preparation of Form II of Efavirenz:

Taken 3 g of Efavirenz in n-butanol (30 ml) and the resulting clear solution was filtered though hy-flow bed to remove undissolved particulate. The solution was cooled to 0-5° C., added water (400 ml) maintained for 1 hr and filtered. The obtained solid was identified as Efavirenz Form II.

XRD showed it to be Form II

While this invention has been described in detail with reference to certain preferred embodiments, it should be appreciated that the present invention is not limited to those precise embodiments rather, in view of the present disclosure, which describes the current best mode for practicing the invention, many modifications and variations, would present themselves to those skilled in the art without departing from the scope and spirit of this invention. This invention is susceptible to considerable variation in its practice within the spirit and scope of the appended claims.

We Claim:

1. A process for preparing (S)-6-chloro-(cyclopropylethynyl)-1,4-dihydro-4-(trifluoromethyl)-2H-3,1-benzoxazin-2-one polymorphic Form β, comprising:
   dissolving efavirenz in a solvent;
   cooling the reaction mass;

seeding the cooled reaction mass containing polymorphic Form β of efavirenz;

adding an anti-solvent; and isolating the pure polymorphic Form β of (S)-6-chloro-(cyclopropylethynyl)-1,4-dihydro-4-(trifluoromethyl)-2H-3,1-benzoxazin-2-one.

2. The process according to claim 1, wherein the step of dissolving efavirenz in the solvent is carried out at room temperature.

3. The process according to claim 1, wherein the solvent is selected from the group consisting of lower aliphatic alcohols, lower aliphatic carboxylic acids, hetero aromatics, polar aprotic solvents, esters, aliphatic hydrocarbons, and mixtures thereof with water.

4. The process according to claim 3, wherein the solvent is selected from methanol, ethanol, isopropyl alcohol, formic acid, acetic acid, ethyl acetate, isopropyl acetate, dimethylformamide, 1-methyl-2-pyrrolidinone and mixtures thereof.

5. The process according to claim 1, wherein the reaction mass is cooled to 0-10° C.

6. The process according to claim 1, wherein the anti-solvent is selected from water, n-heptane or mixtures thereof.

7. A process for preparing (S)-6-chloro-(cyclopropylethynyl)-1,4-dihydro-4-(trifluoromethyl)-2H-3,1-benzoxazin-2-one polymorphic Form β, comprising:

providing a mixture of water and water miscible organic solvent;

dissolving efavirenz into the mixture; and removing the solvent and isolating the polymorphic Form β of (S)-6-chloro-(cyclopropylethynyl)-1,4-dihydro-4-(trifluoromethyl)-2H-3,1-benzoxazin-2-one.

8. The process according to claim 7, wherein the miscible organic solvent is selected from methanol, ethanol, isopropyl alcohol, acetone, and mixtures thereof.

9. The process according to claim 8, wherein the solvent is removed by employing freeze drying or distillation method.

10. The process according to claim 1, wherein the reaction mass is cooled to 0-5° C.

11. The process according to claim 1, wherein the anti-solvent comprises water.

* * * * *